United States Patent [19]

Lüth et al.

[11] Patent Number: 5,766,583

[45] Date of Patent: Jun. 16, 1998

[54] **ISOLATE OF *CONIOTHYRIUM MINITANS* CAMPBELL, COMPOSITIONS AND METHODS OF CONTROLLING PATHOGENIC PLANT FUNGI**

[76] Inventors: Peter Lüth, Fischkaten 48, 23970 Wismar, Germany; Ute Eiben, Inselstr. 24a, 23999 Malchow.Poel, Germany

[21] Appl. No.: 744,085

[22] Filed: Nov. 5, 1996

[30] Foreign Application Priority Data

Jan. 14, 1995 [DE] Germany ............... 195 02 065.0

[51] Int. Cl.⁶ ............... A01N 63/04; C12N 1/14
[52] U.S. Cl. ............... 424/93.5; 435/254.1
[58] Field of Search ............... 424/93.5; 435/254.1, 435/245

*Primary Examiner*—Robert D. Budens
*Attorney, Agent, or Firm*—Schweitzer Cornman Gross & Bondell LLP

[57] ABSTRACT

The invention relates to a novel isolate of *Coniothyrium minitans* Campbell designated CON/M/91-08 having D.S.M. Accession No. DSM-9660. Compositions containing this isolate are suitable for use in methods for controlling pathogenic plant fungi and, in particular, for controlling *Sclerotinia sclerotiorum*.

8 Claims, 4 Drawing Sheets

RAPD Analysis of *Coniothyrium minitans*

Primer DAF8

ISOLATE OF *CONIOTHYRIUM MINITANS* CAMPBELL, COMPOSITIONS AND METHODS OF CONTROLLING PATHOGENIC PLANT FUNGI

This application is a continuation-in-part of international application Ser. No. PCT/DE95/00926 filed Jul. 14, 1995.

FIELD OF THE INVENTION

The present invention relates to a method for controlling pathogenic plant fungi, particularly for controlling Sclerotia-forming plant pathogens, and especially *Sclerotinia sclerotiorum*.

BACKGROUND

The mold, caused by the *Sclerotinia sclerotiorum* pathogen, occurs in many cultivated plants, such as sunflower, tomato, tobacco, lettuce and rape. In some cases, it causes very high losses in yield and during storage.

In most cases, chemical control of the disease is unsatisfactory or not possible at all, since the pathogen survives in the soil in the form of its resting food-storage body, the sclerotia, and infects from there its host plants with the help of various, possible modes of infection.

For example, the fungus, germinates with its fruiting body, the apothecia, from the sclerotia and forms spores, which infect the parts of the plant above ground. On the other hand, fungal mycelia can grow from the sclerotia and are in a position to infect the parts of the plant above as well as below ground.

In the first case a limited extent of chemical control is possible in certain cases, for example, in the case of winter rape. However, until now it has not been possible to control mycelial infections by chemical means.

Through the use of microbial antagonists, which also include *Coniothyrium minitans* and are intended to bring about the destruction of the sclerotia in the soil, it would be possible to replace chemical control. On the other hand, controlling *Sclerotinia sclerotiorum* would become possible in many applications.

There are some products already on the market (biological plant-protective agents), which are based on the action of fungi. The fungi used usually are cultured in a fermenter, large quantities of a fungal biomass or spores or conidia being formed. After being cultured, the fungus is worked up mechanically and subsequently, with the addition of certain materials, formulated as a plant-protective agents. The formulation ensures a good shelf life, as well as a good applicability. Examples of good plant-protective agents are known under the trade name Bio 10 20 sold by Bayer AG, (fungus *Matarhizium anisopliae*); and sold by Makteshim Chemical Works Ltd, under the trade name Trichodex (fungus *Trichoderma harzianum*); GiloMix sold by Kemira Agro Oy (fungus *Gliocladium sp.*)

Conidia or conidia spores are asexually formed spores of fungi. Conidia are formed either by morphologically undifferentiated hyphae or frequently by upright hyphae the conidia carriers, or special structures of the fungi, the receptacles. The conidia of *Coniothyrium minitans* are formed in receptacles, the so-called pycnidia. They are therefore also frequently referred to as pycnidia spores. Pycnidia are hollow, usually spherical or pear-shaped asexual receptacles of fungi. Conidia are formed at the inner wall of the pycnidia and frequently develop on short conidia carriers, which are present in large masses.

Chlamydopores are asexually formed, mostly vat-shaped or pear-shaped fungal spores, which are formed from hyphae cells by a thickening of the cell walls.

Hypha (plural-hyphae) are thread-like organs of certain fungi. In their totality, the hyphae form the fungal mycelia by means of longitudinal growth and branching. A fungus essentially consists of the fungal mycelia. The mycelium, in turn, can assume particular forms, which then constitute the organ of the fungus, such as the receptacles.

Due to longitudinal growth and branching, fungal hyphae can be several meters long and assume a net-shaped structure which is the fungal mycelium. In this form, they are unsuitable for use as a biologically active agent. They are therefore mechanically comminuted. If suitable environmental conditions exist, the fungus can germinate anew from the fragments formed; in other words, it forms new hyphae.

*Coniothyrium minitans* is a fungus, which occurs worldwide naturally in the soil. There are numerous reports of the isolation of this fungus from the sclerotia of *Sclerotina sclerotiorum* and *S. trifoliorum*. Many laboratory and field investigations have shown that *C. minitans* is able to damage the sclerotia of the Sclerotinia species of fungi. There are also publications, such as Trutmann, P., et al., Soil Biology and Biochemistry 12, pp. 461–465 (1980); Tiedemann, A. von, et al., Mitteilungen aus der Biologischen Bundesanstalt für Land- und Forstwirtschaft (Communications from the German Federal Biological Institute for Agriculture and Forestry), Berlin-Dahlem, vol. 301, p. 361 (1994); and Budge, S. P., et al., Plant Pathologie 40, pp. 59–66 (1991) that indicate detection of a reduction in the sclerotia contamination of the soil after an application of *Coniothyrium minitans*.

It is, however, a disadvantage of using *Coniothyrium minitans* that it cannot be applied at this time in a controlled and selective manner.

SUMMARY OF THE INVENTION

It is an object of the present invention to find an isolate of *Coniothyrium minitans* Campbell which is particularly suitable for controlling pathogenic plant fungi, and enables a controlled and selective application.

Such an isolate was identified as the CON/M/91-08 isolate and deposited under the number DSM 9660 with the German Collection of Microorganisms and Cell Cultures in Braunschweig, Federal Republic of Germany.

The effective antagonist can also be applied on the seed, to protect the plant against attack by a disease. This can be accomplished, for example, by coating the seed by using fluidized bed technology. Treatment of the seed with CON/M/91-08 has so far not been carried out. The application of microorganisms on the seed for the purpose of preventing an attack by a disease is, however, known. For example, the company Kemira Agro Oy recommends an agent sold under the Mycostop trade name, which contains the ray fungus, *Streptomyces sp.*, for the treatment of seed. Gufstafson, Inc. sells an agent under the trade name Quantum, in which the spores of *Bacillus subtilis* are formulated also as a seed-treating agent. In addition, there are numerous literature claims in which the use of the microorganisms for protection against plant diseases by means of such application was investigated.

The isolate was recovered as a single spore line from 32 single spore lines and has a particularly high antagonistic activity against *Sclerotinia sclerotiorum* as well as a very good ability to form pycnidia. CON/M/91-08 grows in vitro on different culture media. The isolate is characterized, depending on the culture medium used, at the growth temperature of 22° C. and culturing with exclusion of light, as follows:

| Properties of the culture | Potato dextrose agar | Biomalt agar | Biomalt agar (3 g/l) + yeast | Czapek-dox agar |
|---|---|---|---|---|
| Color of culture | upper side: light gray underside: dirty white with dark brown spots | upper side: dark olive with white to hyaline edge underside: like upper side | upper side: dirty gray, olive towards the center underside: dark olive white edge | upper side: dirty white underside: dark olive with white edge |
| Mycelial shape | supported flat poorly developed mycelium | supported flat, poorly developed mycelium | mycelial layer, 1.0–1.5 mm thick, like absorbent cotton | mycelial layer, up to 1.0 mm thick, fluffy |
| Mycelial growth (n = 100) | 4.6 cm/ 10 days | 4.3 cm/ 10 days | 5.0 cm/ 10 days | 2.2 cm/ 10 days |
| pycnidia formation (n = 50) | 44 pycnidia/cm$^2$ | 82 pycnidia/cm$^2$ | 67 pycnidia/cm$^2$ | 23 pycnidia/cm$^2$ |
| Pycnidia Diameter (n = 50) | 192 μm | 270 μm | 370 μm | 205 μm |
| Conidia Size (n = 100) | 5.27 × 3.51 μm | 6.15 × 4.35 μm | 5.68 × 3.89 μm | 3.98 × 3.72 μm |

In addition, a random amplified polymorphic DNA (RAPD) analysis described e.g. by (Williams et al., 1990, Nucleic Acid Res. 18, 6531), was carried out to detect the CON/M/91-08 isolate. DAF4, DAF6, DAF8 and DAF9 were used as RAPD primers. Random amplified polymorphic DNA RAPD analysis according to Williams et al., 1990, Nucleic Acid Res. 18, 6531 was conducted on some isolates. This generally known analytical technique primarily identifies certain DNA sequences, located between smaller, artificially synthesized nucleotide primary claims with known sequences, and are multiplied with the aid of the polymerase reaction.

Carrier materials are used, to which the fungi are bound, to formulate a fungus for use as a plant protective agent. This formulation should ensure a long shelf life of the fungus with retention of the vitality, as well as good applicability.

Preparations based on the fungal strain CON/M/91-08 (DSM 9960) can be used to combat only pathogens of the Sclerotinia genus and possibly also the species Sclerotium cepivorum. The use of the isolate is therefore intended particularly for controlling the Sclerotinia sclerotiorum and Sclerotinia minor species.

Mutants of the fungal strain CON/M/91-08 (DSM 9660) can be formed if the strain is subjected to a mutagenic treatment (such as irradiation of the fungus with UV light), which results in a mutation, which expresses itself in that genetic information is changed. A new genotype or mutant of the original strain is formed. This mutant can have the same positive properties as CON/M/91-08 but differ in other important properties from the starting strain. Until now, there have not been any mutants of CON/M/91-08.

The Coniothyrium minitans strain of fungus in question was selected from a large number of isolates, which in each case contained a mixture of different genotypes. It represents a genotype, which combines in itself a very good reproducibility, (with solid state fermentation), a very good action against pathogens and an outstanding technical suitability. The term "technical suitability" refers to the robustness of the fungus, which is demonstrated particularly due to the fact that the fungus withstands formulation into a plant-protective agent without much loss in vitality. The action of Coniothyrium minitans as antagonist against certain plant pathogens was known. However, it was not known that different genotypes of the fungus differ from one another with respect to this action and that different genotypes can be selected with respect to further properties as well as combinations of properties.

DESCRIPTION OF THE DRAWING

In the enclosed drawing:

FIG. 3 and 4 respectively show the patterns resulting from the RAPD analyses obtained respectively by using the primers DAF4, DAF6, DAF8, and DAF9.

DETAILED DESCRIPTION

The fungal isolate of the present invention, can be cultured on suitable substrates, such as seeds of grain, bran, straw or other plant materials, or also with the help of agar culture media that are customary in mycology, such as potato dextrose agar, or malt peptone agar, or on suitable support materials to which a culture medium has been added, as well as in liquid nutrient media without the addition of agar.

The present invention also encompasses plant protection agents, which contain the CON/M/91-08 isolate in the form of its pycnidia spores, its mycelia or other fungal components, aside from the usual additives, which help with suspending or formulating practical compositions.

The agents of the present invention can also be used as sprayable solutions or dispersions, emulsifiable concentrates, sprayed powders, dusting agent, seed dressing agent, dispersions, granulates or microgranulates as the active ingredients in the usual compositions.

The conventional, commercial agent, in the form of a concentrate, is generally diluted for use. In the case of water-dispersible granulates, sprayed powders, emulsifiable concentrates, as well as in the case of dispersions, this is suitably done with water. Other formulations, such as dusts, seed dressing preparations or granulates, are usually not to be diluted before use. Under certain circumstances, the agent can also be mixed for use with other, even chemical plant protection agents, such as fungicides, insecticides, herbicides or accaricides, or also with growth regulators or fertilizers.

The invention is further described through the following examples.

EXAMPLE 1

From sclerotia of the Sclerotinia sclerotiorum and Sclerotinia trifoliorum from different locations, numerous isolates of the Coniothyrium minitans fungus were obtained by superficially sterilizing the sclerotia and placing them on an agar culture medium. The fungi, growing out with their mycelia, were determined and all isolates, belonging to the

Figure 1:
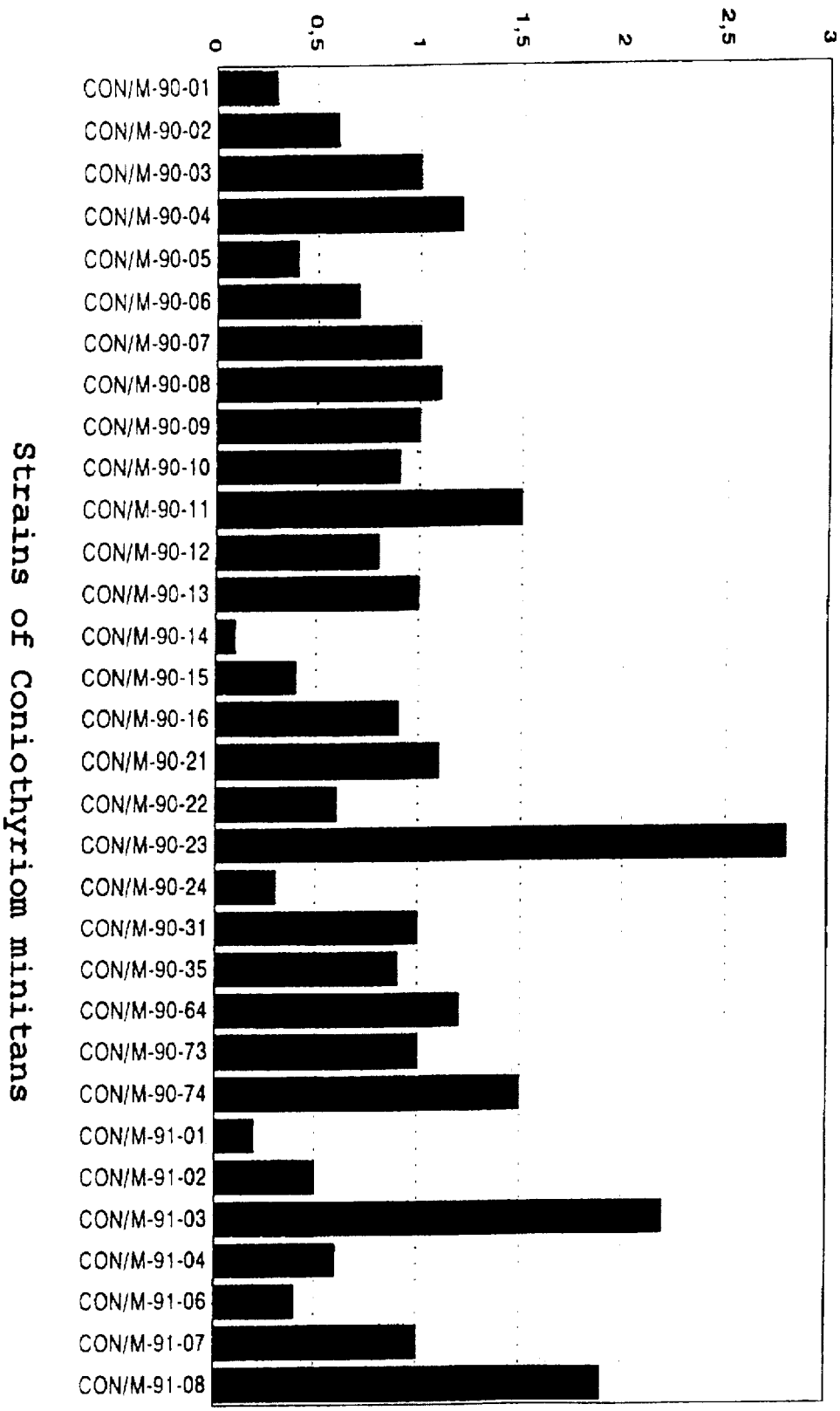
FIG. 1 shows the results of an analysis of Coniothyrium minitans concerning its ability to form pycnidia spores in agar, as a basis for the selection of CON/M/91-08.

*Coniothyrium minitans* species, were accepted in an isolate collection. A selection was carried out with these isolates with respect to their spore-forming ability. This selection took place in two steps. For this purpose, suspensions of pycnidia spores were prepared from the 23 isolates originally obtained and plated out on a biomalt agar, to which yeast extract had been added. After pycnidia formation had commenced on the used agar plates, some colonies were seen to have particularly many well developed pycnidia. From each of these, one pycnidium was obtained and continued as a line. In all, 528 lines were obtained, which were investigated and selected in a subsequent culture on the basis of their pycnidia formation rate. 95 lines were obtained in this manner and were used in a second selection step. In the course of the second selection, single spore lines were obtained from colonies with a particularly strong formation of pycnidia and selected in a subsequent culture. As a result, 32 single spore lines with very good ability to form pycnidia became available. The ability of these lines to form pycnidia spores in agar culture is shown in FIG. 1.

EXAMPLE 2

Figure 2:
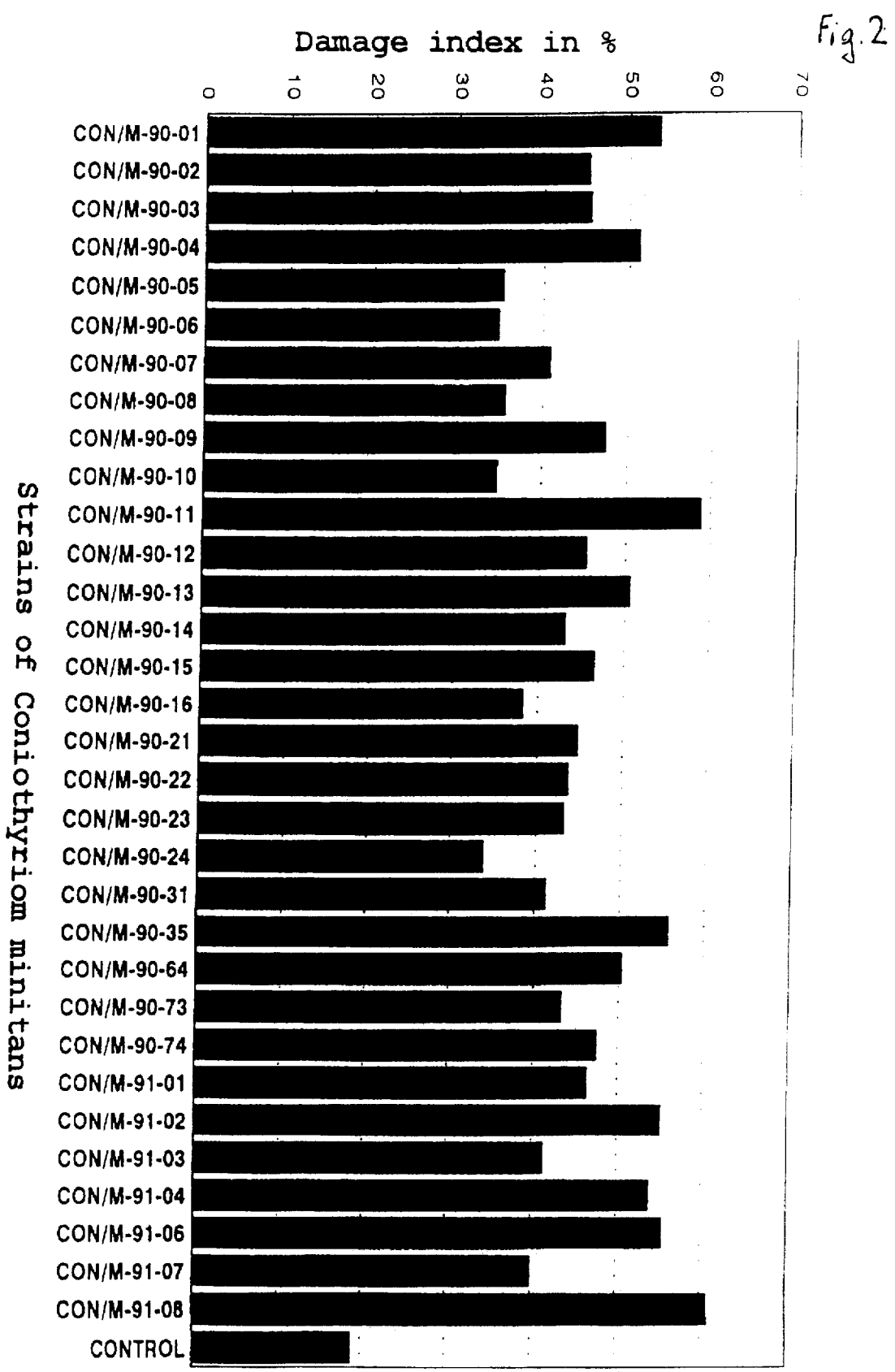
FIG. 2 shows the results of analysis of Coniothyrium minitans concerning the antagonist ability of single spore lines by destruction of the sclerotia, as another basis for the selection of CON/M/91-8.
Figure 4:
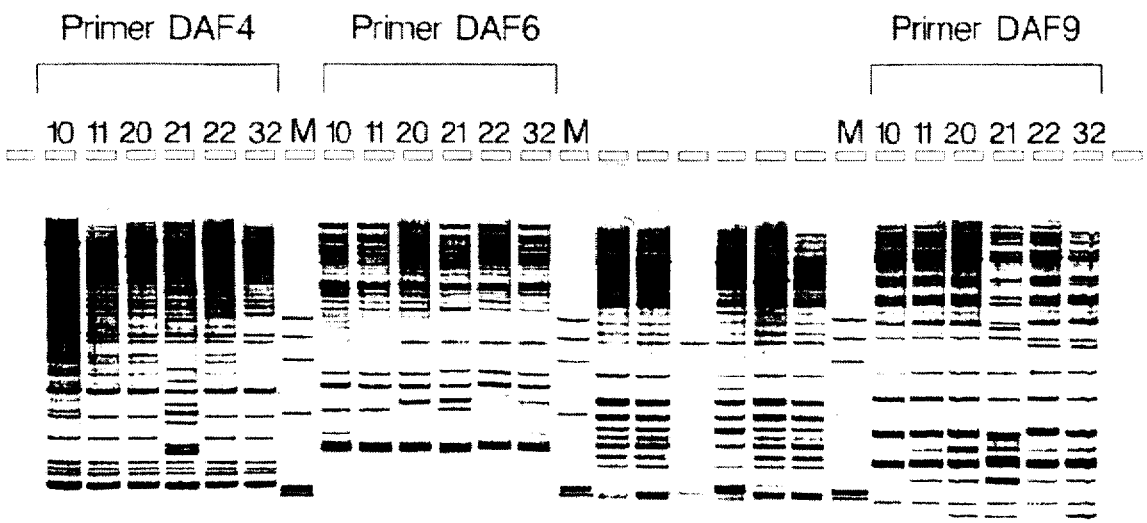

Single spore lines (32) of *Coniothyrium minitans* particularly capable of forming pycnidia, as described in Example 1, were the starting point for the selection of a line, which combines in itself a good ability to form pycnidia with a good antagonistic action. To carry out that selection experimental vessels were filled with quartz sand and moistened with a pycnidia suspension with a concentration of $1\times10^4$ spores/ml. Next, 25 naturally formed Sclerotia obtained from winter rape attacked by *sclerotiorum* were embedded 1 cm deep in four repetitions and incubated in a climatic chamber at 15° C. for 4 weeks, and 12° C. for 8 weeks to simulate the temperature conditions in the soil during the period from mid-August to mid-November. The conditions for the action of the Coniothyrium isolates, which were to be evaluated, were deliberately chosen to be unfavorable, to be able to select those isolates which have a good effect even under unfavorable external influences. The antagonist ability of the single spore lines was evaluated by means of the destruction of the sclerotia at the end of the incubation, as shown in FIG. 2.

The single spore line, CON/M/91-08, with an index of 60.8, brought about the greatest damage to the sclerotia. More than 90% of the sclerotia were damaged, most of them severely.

EXAMPLE 3

After distributing 300 sclerotia per $m^2$ and incorporating them flat by filling into the earth, a suspension of pycnidia, was sprayed onto the surface of the soil in the following variations, and was also incorporated.

| | | |
|---|---|---|
| 1. | CON/M/91-08 | conc.: $1 \times 10^6$ |
| 2. | CON/M/91-08 | conc.: $5 \times 10^6$ |
| 3. | CON/M/91-08 | conc.: $1 \times 10^7$ |
| 4. | VIII 2 Isolate | conc.: $5 \times 10^6$ |

The VIII 2 isolate was an originally obtained isolate, which had not been subjected to any further selection. In each case, 50 ml of suspension per $m^2$ was applied. In addition to the variations, a further variation, which had been infected with *Sclerotinia sclerotiorum* but not treated with antagonists, was run as a control. The test was laid out as a block design with 12 $m^2$ plots in a four-fold repetition. There were spaces left between the plots to reduce to the maximum extent the spreading of the ascospores of *Sclerotinia sclerotiorum* by wind across the borders of the plots.

The evaluation was conducted in July and August of the following year on the basis of the percentage of the disease plants per plot, as well as by means of the plot yield. The results are summarized below:

| Variations | Infested plants | Plot yield kg/plot | % relative to control |
|---|---|---|---|
| CON/M/91-08 ($1 \times 10^6$) | 20.3% | 5.89 | 106.3 |
| CON/M/91-08 ($5 \times 10^6$) | 7.4% | 6.65 | 120.0 |
| CON/M/91-08 ($1 \times 10^7$) | 5.3% | 6.77 | 122.2 |
| VIII 2 Isolate ($5 \times 10^6$) | 18.8% | 5.91 | 106.7 |
| Control | 32.5% | 5.54 | 100.0 |

By incorporating 50 me of the CON/M/91-08 isolate into the uppermost layer of the soil, it was possible to note a distinct reduction in the Sclerotinia infection already at a pycnidia spore concentration of $5\times10^6$ spores/ml. This resulted in a significant increase in the yield of the plot.

EXAMPLE 4

A total of six isolates (isolate 10, isolate 11, isolate 20, isolate 21 (CON/M/91-08), isolate 22, isolate 32) of the *Coniothyrium minitans* fungus were investigated by means of RAPD analyses by TÜV Energie und Umwelt (Energy and Environment), Biological Safety Group with the aim of differentiating isolate 21 from the others.

In a preliminary test, eight RAPD primers were tested for their ability to differentiate between isolate 21 and isolate 22. Three of the primers did not differentiate. Subsequently, the primers DAF4, DAF6, DAF8 and DAF9 were used for the analysis of all isolates.

The patterns, produced with DAF4, and DAF8, differentiated isolate 21 clearly from all others. DAF6 and DAF9 also differentiated between isolate 21 and the others isolates. The latter, however, give different patterns with these primers, which are, in part, similar to the pattern of isolate 21. The electrophoresis gels are shown in FIG. 3.

We claim:

1. An isolated and purified strain of the fungus *Coniothyrium minitans* Campbell designated CON/M/91-08 and having D.S.M. Accession No. DSM-9660.

2. A composition comprising the isolated fungus strain of claim, 1 suspended in a suitable carrier.

3. The composition of claim 2 wherein the isolated fungus strain is in the form of conidia, pycnidia, chlamydospores, fragments of hyphae, or a mixture thereof.

4. A method for controlling pathogenic plant fungi, said method comprising applying the composition of claims 2 or 3 to the fungus or fungal organs to be controlled, or to plant or plant parts bearing the fungus to be controlled, or to seeds which are to be protected against fungal infestation, or to soil containing the fungus to be controlled.

5. The method of claim 4 wherein the composition is applied by spraying a conidia suspension.

6. The method of claim 4 wherein the composition is applied by spraying a pycnidia suspension.

7. The method of claim 4 wherein said pathogenic plant fungus is a sclerotia-forming fungus.

8. The method of claim 7 wherein said pathogenic fungus is *Sclerotinia sclerotiorum*.

* * * * *